US00PP35293P2

(12) United States Plant Patent
Lommerse et al.

(10) Patent No.: US PP35,293 P2
(45) Date of Patent: Aug. 1, 2023

(54) ***BETONICA* PLANT NAMED 'SUMMER GRAPES'**

(50) Latin Name: *Betonica officinalis*
Varietal Denomination: Summer Grapes

(71) Applicant: FUTURE PLANTS LICENTIE B.V., Hillegom (NL)

(72) Inventors: Gerardus Adrianus Petronella Lommerse, Noordwijkerhout (NL); Hendrikus Petrus Lommerse, Lisse (NL)

(73) Assignee: FUTURE PLANTS LICENTIE B.V., Hillegom (NL)

( * ) Notice: Subject to any disclaimer, the term of this patent is extended or adjusted under 35 U.S.C. 154(b) by 0 days.

(21) Appl. No.: 17/983,666

(22) Filed: Nov. 9, 2022

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
CPC ..... A01H 5/02; A01H 5/00; A01H 6/50
See application file for complete search history.

(56) References Cited

PUBLICATIONS

CPVO Register 4.3.55 for Summer Grapes retrieved on Feb. 1, 2023 at https://online.plantvarieties.eu/publicConsultationDetails?registerId=20222026&denomination=summer%20grapes, 2 pp. (Year: 2023).*

* cited by examiner

*Primary Examiner* — June Hwu
(74) *Attorney, Agent, or Firm* — C. Anne Whealy

(57) ABSTRACT

A new and distinct cultivar of *Betonica* plant named 'Summer Grapes', characterized by its relatively compact and broadly upright plant habit; moderately vigorous to vigorous growth habit; dark green-colored leaves; freely flowering habit; relatively long inflorescences with bright purple-colored flowers; and good garden performance.

2 Drawing Sheets

Figure 1:
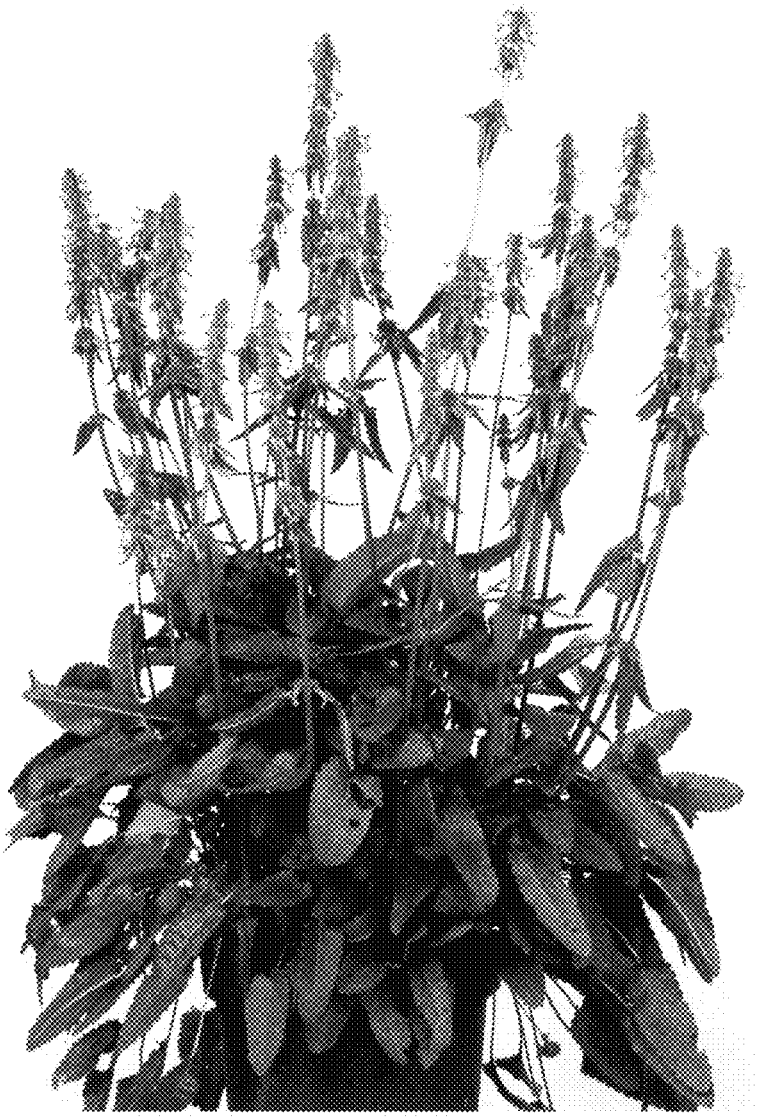

Botanical designation: *Betonica officinalis.*
Cultivar denomination: 'SUMMER GRAPES'.

BACKGROUND OF THE INVENTION

The present invention relates to a new and distinct cultivar of *Betonica* plant, botanically known as *Betonica officinalis*, previously classified as *Stachys officinalis* and *Stachys betonica*, and hereinafter referred to by the name 'Summer Grapes'.

The new *Betonica* plant is a product of a planned breeding program conducted by the Inventors in Lisserbroek, The Netherlands. The objective of the breeding program was to create new compact and freely-flowering *Betonica* plants with unique and attractive flower colors.

The new *Betonica* plant originated from an open-pollination in June, 2016 in Lisserbroek, The Netherlands, of *Betonica officinalis* 'Hummelo', not patented, as the female, or seed, parent with an unknown selection of *Betonica officinalis* as the male, or pollen, parent. The new *Betonica* plant was discovered and selected by the Inventors as a single plant from within the progeny of the stated open-pollination in a controlled environment in Lisserbroek, The Netherlands in June, 2017.

Asexual reproduction of the new *Betonica* plant by divisions in a controlled environment in Lisserbroek, The Netherlands since August, 2017 has shown that the unique features of this new *Betonica* plant are stable and reproduced true to type in successive generations.

SUMMARY OF THE INVENTION

Plants of the new *Betonica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Summer Grapes'. These characteristics in combination distinguish 'Summer Grapes' as a new and distinct *Betonica* plant:

1. Relatively compact and broadly upright plant habit.
2. Moderately vigorous to vigorous growth habit.
3. Dark green-colored leaves.
4. Freely flowering habit.
5. Relatively long inflorescences with bright purple-colored flowers.
6. Good garden performance.

Plants of the new *Betonica* differ primarily from plants of the female parent, 'Hummelo', in plant habit as plants of the new *Betonica* are more compact than and shorter than plants of 'Hummelo'. In addition, plants of the new *Betonica* are more freely flowering than plants of 'Hummelo'.

Plants of the new *Betonica* can be compared to plants of *Betonica officinalis* 'Ukkie', not patented. Plants of the new *Betonica* and 'Ukkie' differ primarily in the following characteristics:

1. Plants of the new *Betonica* have stronger stems than plants of 'Ukkie'.
2. Plants of the new *Betonica* have larger leaves than plants of 'Ukkie'.
3. Plants of the new *Betonica* have longer inflorescences than plants of 'Ukkie'.

4. Plants of the new *Betonica* have bright purple-colored flowers whereas plants of 'Ukkie' have lilac purple-colored flowers.

Plants of the new *Betonica* can also be compared to plants of *Betonica officinalis* 'Pink Cotton Candy', disclosed in U.S. Plant Pat. No. 21,436. Plants of the new *Betonica* and 'Pink Cotton Candy' differ primarily in the following characteristics:

1. Plants of the new *Betonica* are more compact and shorter than plants of 'Pink Cotton Candy'.
2. Leaves of plants of the new *Betonica* have darker green-colored leaves than plants of 'Pink Cotton Candy'.
3. Plants of the new *Betonica* have bright purple-colored flowers whereas plants of 'Pink Cotton Candy' have bi-colored light and bright pink-colored flowers.

BRIEF DESCRIPTION OF THE PHOTOGRAPHS

The accompanying colored photographs illustrate the overall appearance of the new *Betonica* plant showing the colors as true as it is reasonably possible to obtain in colored reproductions of this type. Colors in the photographs may differ slightly from the color values cited in the detailed botanical description which accurately describe the colors of the new *Betonica* plant.

The photograph on the first sheet (FIG. 1) is a side perspective view of typical flowering plant of 'Summer Grapes' grown in a container.

Figure 2:
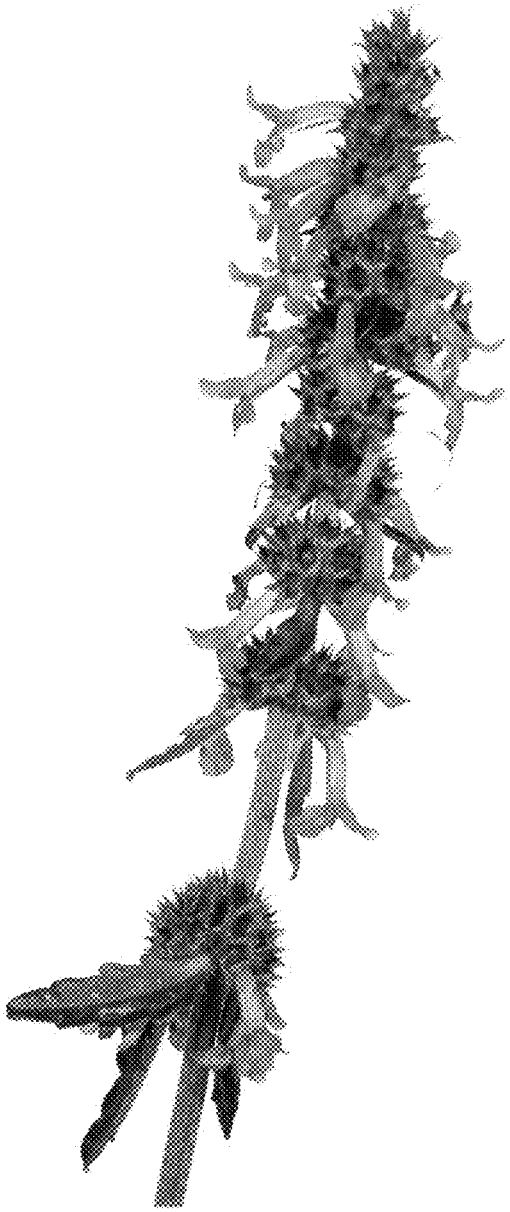

The photograph on the second sheet (FIG. 2) is a close-up view of a typical inflorescence of 'Summer Grapes'.

DETAILED BOTANICAL DESCRIPTION

The aforementioned photographs and following observations, measurements and values describe plants grown during the summer in 19-cm containers in an outdoor nursery in Lisserbroek, The Netherlands and under cultural practices typical of commercial *Betonica* production. During the production of the plants, day temperatures ranged from 18° C. to 30° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Betonica officinalis* 'Summer Grapes'.

Parentage:

*Female, or seed, parent.*—*Betonica officinalis* 'Hummelo', not patented.

*Male, or pollen, parent.*—Unknown selection of *Betonica officinalis*, not patented.

Propagation:

*Type.*—By softwood cuttings.

*Time to initiate roots, summer.*—About one month at ambient temperatures about 25° C.

*Time to produce a rooted young plant, summer.*—About three months at ambient temperatures about 20° C.

*Root description.*—Fine to medium in thickness, slightly fibrous; typically greyed white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a garden plant; relatively compact and broadly upright plant habit; broadly oblong to broadly obovate in overall plant shape; moderately vigorous to vigorous growth habit; moderate growth rate; freely basal branching habit with about 36 primary basal branches developing per plant.

*Plant height, soil level to top of foliar plane.*—About 31 cm.

*Plant height, soil level to top of floral plane.*—About 66 cm.

*Plant width (spread).*—About 53 cm.

*Basal branches.*—Length: About 32.7 cm. Diameter: About 4 mm. Internode length: About 17.5 cm. Shape: Quadrangular. Strength: Strong. Aspect: Upright to slightly outwardly. Texture and luster: Densely pubescent; longitudinally ridged; slightly to moderately glossy. Color, developing: Close to 144A. Color, developed: Close to 143A to slightly darker than 143A; proximally, close to 144B.

Leaf description:

*Arrangement.*—Opposite, simple.

*Length, basal leaves.*—About 10.8 cm.

*Length, cauline leaves.*—About 7 cm.

*Width, basal leaves.*—About 4.6 cm.

*Width, cauline leaves.*—About 2.8 cm.

*Shape, basal and cauline leaves.*—Ovate to narrowly ovate.

*Apex, basal and cauline leaves.*—Obtuse to broadly acute.

*Base, basal leaves.*—Hastate, lobes free to touching.

*Base, cauline leaves.*—Truncate.

*Margin, basal and cauline leaves.*—Crenate.

*Texture and luster, basal and cauline leaves, upper surface.*—Densely pubescent, moderately rugose; slightly glossy.

*Texture and luster, basal and cauline leaves, lower surface.*—Densely pubescent, moderately rugose; matte to slightly glossy.

*Venation pattern, basal and cauline leaves.*—Pinnate.

*Color, basal and cauline leaves.*—Developing leaves, upper surface: Close to 143A. Developing leaves, lower surface: Close to 146B. Fully expanded leaves, upper surface: Close to NN137A; venation, close to 152B. Fully expanded leaves, lower surface: Close to 147B; venation, close to 145B.

*Petioles.*—Length, basal leaves: About 23.1 cm. Length, cauline leaves: About 2.6 cm. Diameter, basal and cauline leaves, flattened: About 2.5 mm. Texture and luster, basal and cauline leaves, upper and lower surfaces: Moderately pubescent; moderately glossy. Strength, basal and cauline leaves: Strong. Color, basal and cauline leaves, upper surface: Close to 144B. Color, basal and cauline leaves, lower surface: Close to 144A.

Flower description:

*Flower type, arrangement and habit.*—Single tubular labiate flowers arranged on relatively long terminal racemes; flowers sessile; freely flowering habit with about 200 flowers developing per inflorescence and about 7,200 flowers developing per plant during the flowering season; flowers with an upper lip and a three-lobed lower lip; flowers face mostly outwardly on the raceme.

*Natural flowering season*.—Plants flower for about ten weeks during the summer in The Netherlands.

*Flower longevity on the plant*.—Individual flowers last about one week on the plant; flowers not persistent.

*Fragrance*.—None detected.

*Flower buds*.—Length: About 8 mm. Diameter: About 2 mm. Shape: Oblong. Texture and luster, sepals: Densely pubescent; matte. Texture and luster, petals: Smooth, glabrous; matte. Color, sepals: Close to 145C; distally, close to 137A and tinged with close to N77B. Color, petals: Close to 77D; distally, close to 77B.

*Inflorescence height*.—About 20.9 cm.

*Inflorescence diameter*.—About 3.2 cm.

*Flower diameter*.—About 6 mm by 9 mm.

*Flower length*.—About 1.5 cm.

*Flower throat diameter*.—About 2 mm.

*Flower tube length*.—About 1 cm.

*Flower tube diameter*.—About 2.5 mm.

*Petals*.—Quantity and arrangement: One upper lip and one three-lobed lower lip; lower 60% of the petals are fused into a narrow tube. Length, upper and lower lips, free part: About 4 mm. Width, upper lip: About 3 mm. Width, lower lip: About 6 mm. Shape, upper lip: Broadly ovate. Shape, lower lip: Broadly obovate. Apex, upper lip: Obtuse. Apex, lower lip: Praemorse. Margin, upper lip: Entire, not undulate. Margin, lower lip: Entire, moderately undulate; lateral lobes recurved. Texture and luster, upper and lower lips, inner surface: Smooth, glabrous, slightly velvety; matte. Texture and luster, upper lip, outer surface: Densely pubescent, slightly velvety; matte. Texture and luster, lower lip, outer surface: Smooth, glabrous and towards the base, densely pubescent, slightly velvety; matte. Texture, throat: Smooth, glabrous. Texture, tube: Densely pubescent. Color, upper lip: When opening and fully opened, inner surface: Close to N78A to N78B; venation, close to N80A. When opening and fully opened, outer surface: Close to N80B; venation, close to N81A. Color, lower lip: When opening and fully opened, inner surface: Close to N78B; venation, close to N80A. When opening and fully opened, outer surface: Close to 77D; towards the apex, close to N80B; venation, close to N81A. Color, throat: Close to N78B; venation, close to N80A. Color, tube: Close to N80B; venation, close to N80B.

*Sepals*.—Quantity and arrangement: Five, lower 70% fused into a tubular calyx. Calyx length: About 5 mm. Calyx diameter: About 3 mm. Length: About 5 mm. Width: About 1 mm. Shape: Narrowly oblong. Apex: Narrowly acute. Margin: Entire. Texture and luster, upper surface: Smooth, glabrous; matte. Texture and luster, lower surface: Moderately pubescent; matte. Color: When opening, upper and lower surfaces: Close to 145C; distally, close to 137A tinged with close to N77B. Fully opened, upper and lower surfaces: Close to 145B; distally, close to 138A tinged with close to N77B.

*Peduncles*.—Length: About 33.8 cm. Diameter: About 3.5 mm. Aspect: Mostly upright. Strength: Strong. Texture and luster: Densely pubescent; slightly glossy. Color: Close to 143A.

*Reproductive organs*.—Stamens: Quantity per flower: Four. Filament length: About 2 mm to 3 mm. Filament color: Close to N82C. Anther shape: Narrowly elliptic; dorsifixed. Anther size: About 0.5 mm by 1 mm. Anther color: Close to 166C. Pollen amount: Scarce. Pollen color: Close to N155A. Pistils: Quantity per flower: One. Pistil length: About 1 cm. Stigma diameter: About 1 mm. Stigma shape: Cleft. Stigma color: Close to N81B. Style length: About 1 cm. Style color: Close to N81B; proximally, close to N81D to lighter than N81D. Ovary color: Close to 152C to 152D.

*Seeds and fruits*.—To date, seed and fruit production have not been observed on plants of the new *Betonica*.

Pathogen & pest resistance: To date, plants of the new *Betonica* have not been observed to be resistant to pathogens and pests common to *Betonica* plants.

Garden performance: Plants of the new *Betonica* have exhibited good tolerance to rain, wind and temperatures ranging from about −29° C. to 35° C. and to be suitable for USDA Hardiness Zones 4 to 9.

It is claimed:

1. A new and distinct *Betonica* plant named 'Summer Grapes' as illustrated and described.

* * * * *